United States Patent
Fukushima et al.

(10) Patent No.: US 7,479,362 B2
(45) Date of Patent: Jan. 20, 2009

(54) UV DECOMPOSABLE MOLECULES AND A PHOTOPATTERNABLE MONOMOLECULAR FILM FORMED THEREFROM

(75) Inventors: Hitoshi Fukushima, Fujimi-cho (JP); Hiroshi Takiguchi, Fujimi-cho (JP); Tatsuya Shimoda, Fujimi-machi (JP); Takashi Masuda, Suwa (JP); Richard James Bushby, Leeds (GB); Stephan Evans, Leeds (GB); J.P. Jeyadevan, Jaffna (LK); Kevin Critchley, Leeds (GB)

(73) Assignee: Seiko Epson Corporation, Tokyo (JP)

( * ) Notice: Subject to any disclaimer, the term of this patent is extended or adjusted under 35 U.S.C. 154(b) by 432 days.

(21) Appl. No.: 11/116,265

(22) Filed: Apr. 28, 2005

(65) Prior Publication Data
US 2005/0245739 A1    Nov. 3, 2005

(30) Foreign Application Priority Data
Apr. 29, 2004   (GB)   ................................. 0409606.1
Oct. 7, 2004    (JP)   ............................. 2004-295100

(51) Int. Cl.
G03F 7/00    (2006.01)
G03F 7/004   (2006.01)

(52) U.S. Cl. .................... 430/270.1; 430/311; 430/915; 430/935; 540/350

(58) Field of Classification Search .............. 430/270.1, 430/270.15, 311, 935, 915; 540/350
See application file for complete search history.

(56) References Cited

U.S. PATENT DOCUMENTS 4,400,461 A * 8/1983 Chandross et al. .......... 430/311

(Continued)

FOREIGN PATENT DOCUMENTS

EP    0 046 025 A3    2/1982

(Continued)

OTHER PUBLICATIONS

Critchley et al, "A Mild Photoactivated Hydrophilic/Hydrophobic Switch", Langmuir 2005, 21, 4554-4561.*

(Continued)

Primary Examiner—Amanda C. Walke
(74) Attorney, Agent, or Firm—Oliff & Berridge, PLC

(57) ABSTRACT

Aspects of the invention provide a method of controlling the solid-state property of the solid-phase surface or controlling forming reactive region. The method can be attained by using a device for ejecting droplets and a molecule for inclusion in a SAM which can be photo-patterned in a short period of time using low energy UV radiation, that is TV radiation having a relatively long wavelength. The invention can provide monomolecular film that is formed from molecules comprising a structural component (B) which is hydrophobic and/or lipophobic, and a structural component (A) which decomposes when irradiated with UV light having a wavelength in the range 254-400 nm to cleave away a part of the molecule having the structural component (B) leaving a residual hydrophilic structural component (C). Further, the invention can provide a method of forming a film pattern comprising: at least a step of ejecting a droplet, which includes a compound represented as the following Formula (0), on a solid-phase surface having a functional moiety:

X—Y-Z    (0)

where, X represents a structure having reactivity to a functional moiety which exists at the solid-phase surface, Y represents a decomposable structure by itself and Z represents a structure which is capable of changing solid-state properties on the solid-phase surface or a reactive structure.

28 Claims, 8 Drawing Sheets

U.S. PATENT DOCUMENTS

| | | | |
|---|---|---|---|
| 6,057,096 | A | 5/2000 | Rothschild et al. |
| 7,098,525 | B2 * | 8/2006 | Bai et al. .................. 257/642 |

FOREIGN PATENT DOCUMENTS

| | | |
|---|---|---|
| JP | 10-500409 A | 1/1998 |
| JP | A 10-077257 | 3/1998 |
| JP | 2003-321479 A | 11/2003 |
| JP | 2004-051624 A | 2/2004 |
| JP | 2004-231590 A | 8/2004 |
| WO | WO 03/006625 A3 | 1/2003 |

OTHER PUBLICATIONS

Sugiura, Hiroyuki, "Scanning Probe Lithography", pp. 1182-1186 with partial translation.

Dunkin, Ian R. et al., "Photoautomersion of o-nitrobenzyl compounds: o-quinonoid *aci*-nitro species studied by matrix isolation and DFT calculations", Perkin Trans. 2, 2001, pp. 1414-1425.

Hong, Lan et al., "Micropatterning of organosilane self-assembled monolayers using vacuum ultraviolet light at 172 nm: resolution evaluation by Kelvin-probe force microscopy", Surface and Coatings Technology, 169-170 (2003) pp. 211-214.

Pease, Ann Caviani et al., "Light-generated oligonucleotide arrays for rapid DNA sequence analysis", Proc. Natl. Acad. Sci. USA, vol. 91, pp. 5022-5026, May 1994, Biochemistry.

Zhao, Bin et al., "Principles of Surface-Directed Liquid Flow in Microfluidic Channels", Analytical Chemistry, 2002, vol. 74(16), pp. 4259-4268 and Chemical Abstracts, abstr No. 137:175408.

Harkness, Brian R., et al., "A Directly Photo-Patternable Spin-on-Glass Based on Hydrogen Silsesquioxane and Photobase Generators", Polymer Preprints, 1998, vol. 39(1), pp. 493-494 & Chemical Abstracts, Ab. No. 128-263823.

* cited by examiner

UV DECOMPOSABLE MOLECULES AND A PHOTOPATTERNABLE MONOMOLECULAR FILM FORMED THEREFROM

BACKGROUND

Aspects of the invention can relate to certain molecules which are susceptible to decomposition by UV light particularly those having a hydrophobic and/or lipophobic structural component. Such molecules may be used to form a monomolecular film which can be photo-patterned when image-wise exposed to low energy UV irradiation. Further, the invention relates a method of forming a film pattern using a technique of discarding tiny droplets such as an ink-jet method, particularly a method of forming a film pattern which is capable of changing solid-state property of the solid-phase surface, or a method of forming a film pattern having reactivity.

Related art methods for forming patterned films on substrate, such as semiconductor substrates can include methods based upon dissolving a photosensitive polymer material in a solvent and then forming a film of this material by spin coating on a semiconductor substrate. The resulting film is then irradiated with ultraviolet rays (UV) through a patterned mask resulting in the formation of a negative or a positive pattern in the photosensitive polymer film. However, the technique of spin coating is inefficient insofar as up to 99% by weight of the polymer material is discarded during the coating step.

As an improvement of such processes, it has been proposed to form photopatternable films of monomolecular thickness which can be imaged by exposure to UV irradiation. These films are called Self-Assembled Monolayers (SAMs). Examples of such methods are disclosed in Micropatterning of organosilane self-assembled monolayers using vacuum ultraviolet light at 172 nm: resolution evaluation by Kelvin-probe force microscopy by H. Sugimura et al., pages 169-170 in Surface Coating Technology (2003) and Scanning probe nanolithography by H. Sugimura page 1182 of Vol. 70, in OYO BUTURI (Applied physics in Japan). Methods using SAMs reduce wastage of the photopatternable material compared to processes which make use of spin coating. This is because only a very small amount of photosensitive material is needed, i.e., the amount needed to form a monomolecular film of the material.

However, the previously proposed photopatternable SAMs have the disadvantage that they have needed to be exposed to high energy UV irradiation for a long period of time in order to be satisfactorily imaged. This means that they have relatively poor processing efficiency. It is desirable therefore to provide an improved material for forming a SAM which can be photo-patterned by exposure to low energy UV irradiation, that is by exposure to UV light having a relatively long wavelength, for a short period of time.

Separately from the above, Dunkin et al, disclose in J. Chem. Soc. Perkin Trans. 2, (2001), page 1414 page 1414 in J. Chem. Soc., Perkin Trans.2, (2001) that an o-nitrobenzyl ester derivative absorbs UV radiation at approximately 254 nm. This absorption induces photoisomerization and photodecomposition reactions.

This is illustrated in the following reaction scheme:

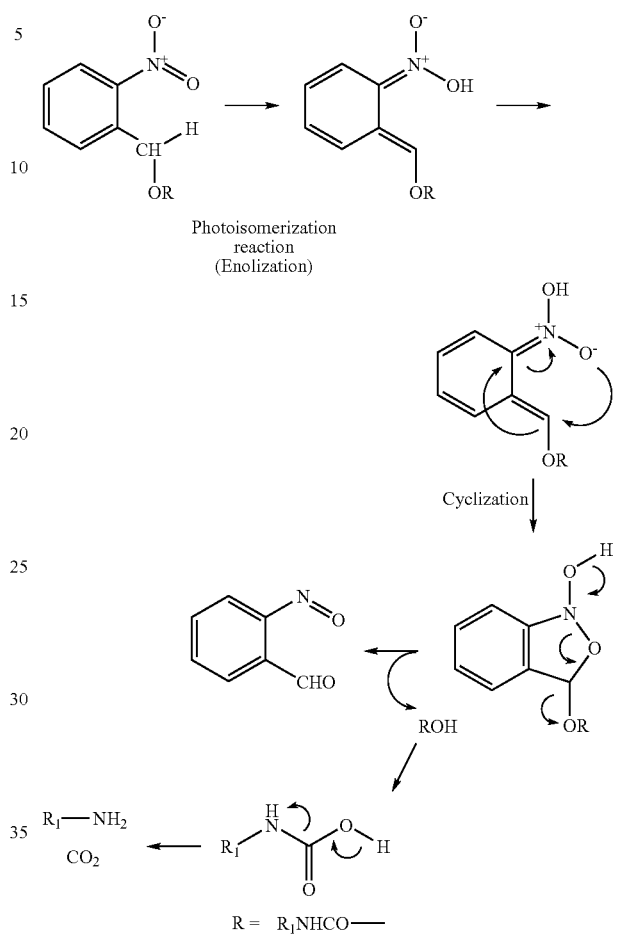

The first reaction in the above scheme is the intramolecular enolization reaction of an o-nitrobenzyl ester derivative. This enolization reaction in turn induces intramolecular cyclization. An ester group present at the benzyl group then dissociates thereby forming a compound having an aldehyde and a nitroso group as a decomposition product. When a carbamic ester linkage is formed at the benzyl group, an amine compound and carbon dioxide are also formed as the other decomposition products.

The present inventors had the idea that derivatives of this type including a photodegradable structural component could be incorporated into a SAM useful for photo-patterning which could be formed on a variety of different substrate types. They further had the idea that such a SAM could be arranged to express two different surface properties of on the one hand hydrophobicity and/or lipophobicity and on the other hand hydrophilicity by means of careful molecular design such that when the molecule is subjected to UV irradiation, the hydrophobic and/or lipophobic structural component is cleaved away liberating a hydrophilic substituent.

In recent years, a technology is required in which DNA, a biological molecule such as antibody and compounds having reactivity with them are fixed onto a solid-phase surface with high dense and high accurate pattern so as to develop a biosensor detecting a specific biological molecule from a test sample and lab-on-chip technology implementing micro-sized biochemical experiments on a glass chip.

As a method of fixing DNA onto a substrate surface with high density, it has been proposed in the pages 5022 to 5026 in *Proceedings of the National Academy of Sciences*. Vol. 91(1994) by Pease, A. et al. that light is irradiated on a self-assembled monomolecular film having an photo-cleaved protective group with using a photo mask for example forming a pattern of a hydroxyl group, which is specifically reactive, then compounds having four different bases are reacted each other extending one DNA chain.

A method using a photo mask, however, faces difficulty in adjustment of alignment at the time of exposure reaction, resulting in low yield and high manufacturing cost with insufficient detecting sensitivity. On the other hand, as a method of forming tiny film pattern on a surface of solid substrate, a means of ejecting micro droplets such as ink-jet method is used. The device for ejecting micro droplets enables a material included in a droplet to be supplied to a specific position on the substrate by ejecting a droplet with moving a stage on which a solid phase group is installed.

Therefore, in such case when biological molecules or compounds are fixed with giving direct pattern, it is efficient that pre-processes such as forming a region being reactive with these biological molecules or compounds and controlling a solid-state property such as wettabililty, are implemented to a surface of a substrate. According to such processes, preferably trapping a material to be fixed in a targeted region and preventing it from being attached to other region can be possible.

SUMMARY

Aspects of the invention can provide a molecule for inclusion in a SAM which can be photo-patterned in a short period of time using low energy UV radiation, that is UV radiation having a relatively long wavelength.

Aspects of the invention can provide such a molecule which can be formed into various types of SAMs and used for photo-patterning a variety of different types of substrates.

Aspects of the invention can further provide a SAM having two different surface properties, that is initially a hydrophobic and/or lipophobic property but which is converted to a hydrophilic property on UV irradiation.

A fourth object of the invention can also provide a method for controlling a slid state property of a solid-phase surface using a means of ejecting a droplet and a method of controlling the formation of a reactive region.

These objects may be attained by introducing a structural component in a SAM which is decomposed when irradiated with UV light having a wavelength in the range 254-400 nm causing cleavage of the molecule while at the same time also including a structural component in the SAM which is hydrophobic and/or lipophobic. Therefore, according to an aspect, the invention provides a molecule comprising a structural component (A), which decomposes when irradiated with UV light having a wavelength in the range 254-400 nm, and a structural component (B) which is hydrophobic and/or lipophobic.

It is preferred that the structural component (A) is an o-nitrobenzyl ester. This structural component has the advantage of being easily cleaved when irradiated with low energy UV light having a relatively long wavelength well within the range of 254-400 nm. It is preferred also that the terminal group bonded to the benzyl group of the o-nitrobenzyl ester should be a succinic imides. This structural component has the advantage of allowing the molecule to be coupled by covalent bonding either directly to a substrate surface having suitable functional groups or via a monolayer of a coupling compound previously attached to the substrate surface and which has a functional group reactive with a succinic imide residue.

The structural component (B) is preferably a fluorinated chain which more preferably may be saturated. The chain may be straight or branched. Further the chain may also be perfluorinated which has the advantage of increasing the chain's hydrophobicity.

In this first aspect of the present invention, the molecule preferably has the general Formula (I):

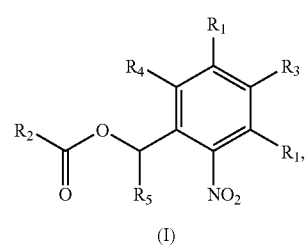

[Formula 6]

(I)

wherein:

$R_1$ independently represents a hydrogen atom, —$OR_6$ ($R_6$ is an alkyl chain having a carbon number of 1 to 10), —NH(CO)$R_7$ ($R_7$ represents an alkyl chain having a carbon number of 1 to 10, or an alkyl fluoride chain having a carbon number of 1 to 10), N($R_8$)$_2$ ($R_8$ represents an alkyl chain having a carbon number of 1 to 5) or —S($R_9$) ($R_9$ represents an alkyl chain having a carbon number of 1 to 10). $R_2$ represents an N-hydroxy succinic imide group (optionally substituted with a sulfonyl group). $R_3$ represents —$X_2$—(CH$_2$)$_n$—$X_1$, wherein $X_2$ represents —CH$_2$— or —O—, n is 0 or an integer of 1 to 10, and $X_1$ represents —OZ, -Z or

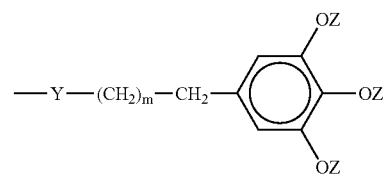

wherein, Y represents —(CH$_2$)— or —O—, Z represents a fluoroalkyl group having a carbon number of 1 to 20 and m represents 0 or an integer of 1 to 10; $R_4$ represents —NO$_2$ or a hydrogen atom; and $R_5$ is a hydrogen atom or an alkyl group having a carbon number of 1 to 10.

Preferably the substituent $R_1$ is a methoxy group. The presence of the substituent $R_1$ has the advantage of causing the o-nitrobenzyl ester structural component to absorb UV light in the region 330-360 nm, that is UV light of very low energy.

Preferred fluoroalkyl groups having a carbon number of 1 to 20 represented by Z include —(CH$_2$)$_m$(CF$_2$)$_p$F or a branched chain isomer thereof wherein m is as defined above and p is 0 or an integer of 1 to 9.

A preferred molecule of the above general Formula is:

[Formula 7]

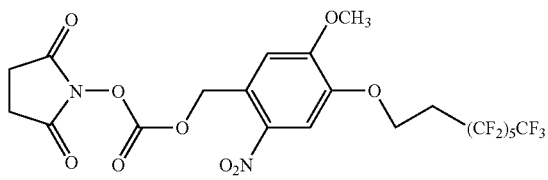

According to another aspect, the invention provides a monomolecular film coated substrate. The film is formed from molecules including a structural component (B) which is hydrophobic and/or lipophobic, and a structural component (A), which decomposes when irradiated with UV light having a wavelength in the range 254-400 nm to cleave away a part of the molecule including the structural component (B) leaving a residual hydrophilic structural component (C).

In the same way as in the above aspect, it is preferred that the structural component (A) is an o-nitrobenzyl ester, and that the structural component (B) comprises a fluorinated chain which may more preferably be saturated. The fluorinated chain may also be branched and/or perfluorinated.

It is preferred that the hydrophilic structural component (C) includes an amine group or a hydroxyl group. Such groups are advantageous insofar as they can react with a succinic imide to covalently bond with molecules in accordance with the first aspect of the present invention but then cleave when irradiated with UV irradiation to liberate the relatively hydrophilic amine group or hydroxyl group.

The monomolecular film (SAM) of an aspect is obtainable by coating a substrate with a monomolecular film of a coupling compound (D) which has a hydrophilic moiety and subsequently reacting the hydrophilic moiety-with a molecule according to the first aspect of the present invention. The substrate may be any suitable material, including a metal, a semiconductor or a plastic.

Alternatively, the monomolecular film (SAM) coating the substrate may be formed entirely from the molecules according to the first aspect of the present invention if these molecules are able to satisfactorily adhere to the substrate for instance by means of covalent bonding to suitable pre-existing functional groups on the substrate surface. This formation can in particular be the case if the substrate has a hydrophilic surface.

According to an aspect, the invention can provide a method of photo-patterning the monomolecular film coated substrate according to the second aspect described above. The method can include the step of image-wise irradiating the monomolecular film coated substrate with UV light having a wavelength in the range 254-400 nm through a patterned mask to cleave the coated molecules at the structural component (A) thus removing the structural component (B) from the coated film in the irradiated areas converting them from being hydrophobic and/or lipophobic to hydrophilic.

Further, in order to solve the aforementioned issues attaining the above object of the invention, the inventors found as the result of extensive research a compound including the structural component X, which is reactive with functional group on a solid surface, the structural component Z, which changes a solid-state property of a solid-phase surface and the structural component Y, which is decomposable and located between X and Z. The compound is applied to the solid-phase surface by ejecting micro droplets controlling solid-state property of the solid-phase surface in line with a fine pattern. In the above compound, Z is made to be a reactive structural component forming a reactive region with fine patterns on the solid-phase surface.

Further, they found that Y is decomposed after fixing the above compound onto the solid-phase surface once, returning solid-state property or reactivity of the solid-phase surface to the original state and Y is also decomposed giving different solid-state property or reactivity by a functional moiety exposed on the surface.

Namely, according to an aspect, the invention can relate to a method [1] of forming a film pattern comprising; at least a step of ejecting a droplet, which includes a compound represented as the following Formula, on a solid-phase surface having a functional moiety:

X—Y—Z (O)    [Formula 8]

Here, X represents a structural component having reactivity with a functional moiety, which exists at the solid-phase surface, Y represents a decomposable structural component by itself and Z represents a structural component which is capable of changing solid-state properties on the solid-phase surface or a reactive structural component. Further the invention includes the method [1] in which the solid-state property is wettability. Or the invention relates to a method [3] based on [1] or [2], wherein Z includes a structural component, which is selected from any of groups including a saturated or unsaturated alkyl chain capable of having a substituent, a saturated or unsaturated fluorinated chain capable of having a substituent, hydoxyl group, amino group, urethane group, carboxyl group, carbonyl group, urea group, sulfonic group, disulfide group, epoxy group, carbodiimide group, maleimido group, N-hydroxy succinic imide group. Or the invention relates to a method [4] based on any of [1] to [3], wherein X includes a structural component, which is selected from any of groups including amino group, urethane group, carboxyl group, carbonyl group, urea group, sulfonic group, disulfide group, epoxy group, carbodiimide, group, maleimido group, alkoxy silane, silane halide, and N-hydroxy succinic imide group. Or the invention relates to a method [5] based on any of [1] to [4], wherein Y is a structural component having a property of optical response. Or the invention relates to a method [6] based on [1], where the compound is expressed as the following Formula:

[Formula 9]

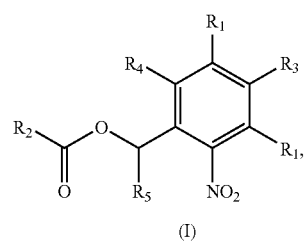

(I)

wherein, $R_1$ independently represents a hydrogen atom, —$OR_6$ ($R_6$ is an alkyl chain having a carbon number of 1 to 10), —NH(CO)$R_7$ ($R_7$ represents an alkyl chain having a carbon number of 1 to 10, or an alkyl fluoride chain having a carbon number of 1 to 10), N($R_8$)$_2$ ($R_8$ represents an alkyl chain having a carbon number of 1 to 5) or —S($R_9$) ($R_9$ represents an alkyl chain having a carbon number of 1 to 10).

$R_2$ represents an N-hydroxy succinic imide group (optionally substituted with a sulfonyl group. $R_3$ represents —$X_2$—

$(CH_2)_n$—$X_1$, wherein $X_2$ represents —$CH_2$— or —O—, n is 0 or an integer of 1 to 10, and $X_1$ represents —OZ, -Z or

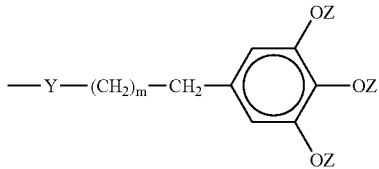

wherein, Y represents —$(CH_2)$— or —O—, Z represents a fluoroalkyl group having a carbon number of 1 to 20 and m represents 0 or an integer of 1 to 10; $R_4$ represents —$NO_2$ or a hydrogen atom; and $R_5$ is a hydrogen atom or an alkyl group having a carbon number of 1 to 10.

Or the invention can relate to a method [7] based on any of the above [1] to [6], which further can include a step of fixing a compound having a functional moiety, which is capable of bonding X, onto the solid-phase surface before ejecting a liquid including a compound represented as the Formula. Or the invention relates to a method [8] based on any of the above [1] to [7], wherein the method of ejecting droplets is an inkjet method. Or the present invention relates to a method [9] based on any of the above [8] to [1], wherein the droplets include a solvent, which is selected from any of groups such as water, ethanol, DMF, DMSO, HMPA, pyrrolidone group, dioxane. Or the invention relates to a method [10] based on any [1] to [9], wherein the method of ejecting droplets includes a means of controlling to dry the droplet.

EFFECTS OF THE INVENTION

According to aspects of the invention, it can provide a molecule for inclusion in a SAM, which can be photo-patterned in a short period of time using low energy UV radiation, that is UV radiation having a relatively long wavelength. Further, the invention can provide such a molecule, which can be formed into various types of SAMs and used for photo-patterning a variety of different types of substrates. The invention can also provide a SAM having two different surface properties, that is initially a hydrophobic and/or lipophobic property but which is converted to a hydrophilic property on TV irradiation.

According to the invention, a compound including a first structural component, which is reactive with functional moiety on a solid-phase surface, a second structural component, which changes a solid-state property of a solid-phase surface, and a third structural component, which is located between the first and the second structural components and decomposable, is ejected as a solution onto the solid-phase surface. It is possible to control the solid-state property of the solid-phase surface in line with minute patterns. It is also possible to control the formation of a reactive region. Further, the decomposition of the above third structural component, which is decomposable, can allow a solid-state property and a reactivity, which have been given to the solid-phase surface once, to be returned to the original state or a new solid-state property and a new reactivity to be given to the solid-phase surface by a functional moiety, which has been exposed to the surface through the decomposition.

BRIEF DESCRIPTION OF THE DRAWINGS

The invention will be described with reference to the accompanying drawings, wherein like numerals reference like elements, and wherein.

DETAILED DESCRIPTION OF PREFERRED EMBODIMENTS

Figure 1:
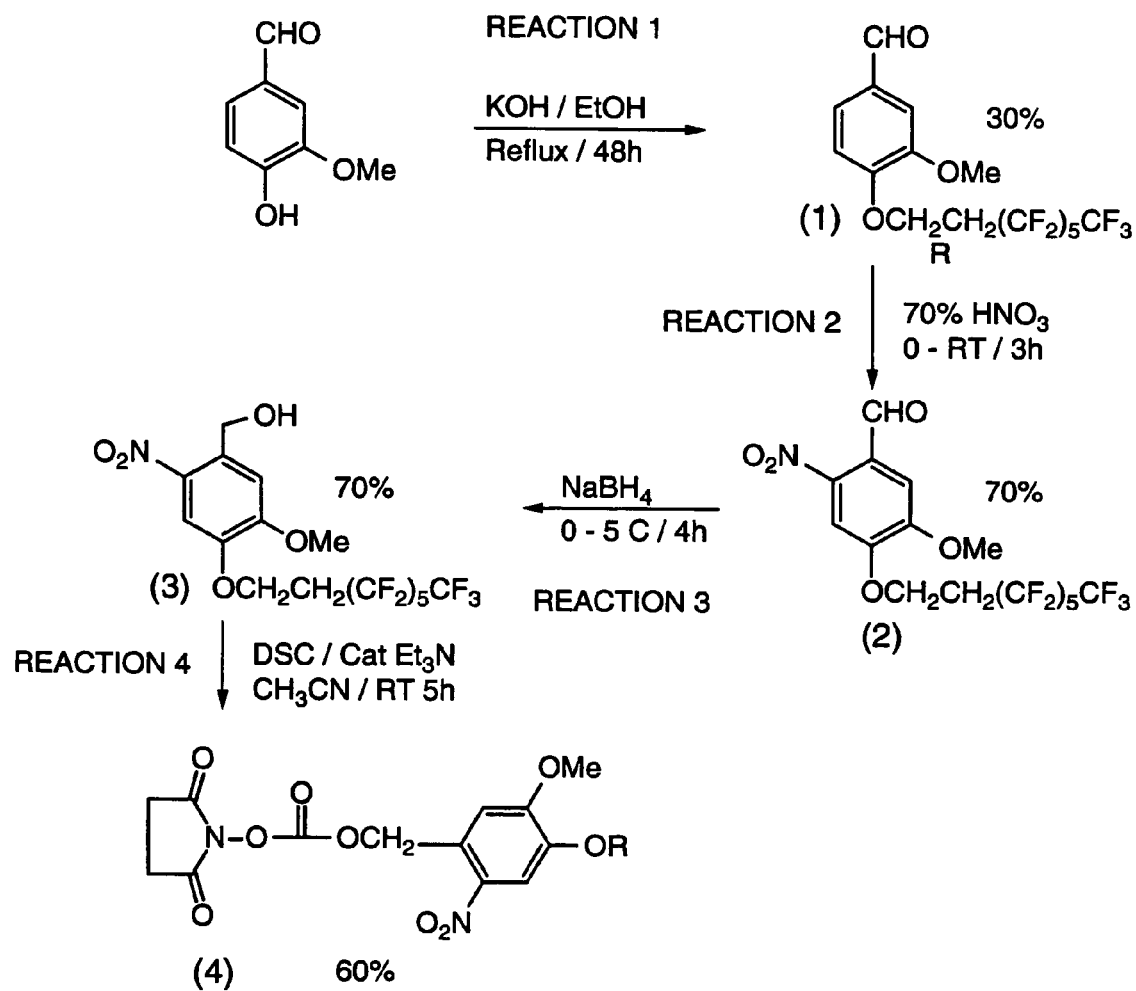
FIG. 1 shows the synthesis of a molecule (compound 1) according to the first aspect of the invention.

Exemplary embodiments of the invention will now be described with reference to the accompanying drawings.

Returning to the first aspect of the invention as discussed above, this relates in its broadest aspect to a molecule comprising a structural component (A) which decomposes when irradiated with UV light having a wavelength in the range 254-400 nm, and a structural component (B) which is hydrophobic and/or lipophobic. Thus the molecule can include at least two separate structural components. The first of these structural components, labeled (A), is a chemical structure or moiety which decomposes when irradiated with UV light having a relatively long wavelength which falls in the range 254-400 nm. This structural component renders the molecule sensitive to TV light and thus makes the molecule itself, or a larger molecule that is sensitive to UV light and therefore capable of being photo-patterned. The structural component (A) is coupled into the larger molecule. On the other hand, the structural component (B) is hydrophobic and/or lipophobic resulting in the molecule itself having this property or these properties. As a consequence, a monomolecular film formed from the molecules of the first aspect of the invention has a hydrophobic and/or lipophobic surface property. The property is also possessed by a monomolecular film (SAM), which is formed by coupling the molecules of the first aspect of the invention to a monomolecular film of a coupling compound already coated on a substrate.

Molecules in accordance with the first aspect of the invention can be photo-patterned even when irradiated for a short period of time such as 10 seconds to 10 minutes, more preferably 30 seconds to 5 minutes, most preferably 1 to 5 minutes with low energy UV light corresponding to a wavelength in the range 254-400 nm. This means that photo-patterning can be carried out relatively efficiently insofar as it requires only relatively low energy irradiation.

The structural component (A) which can be decomposed when irradiated with UV light may be an o-nitrobenzyl ester.

The decomposition of such a structural component is set out above in relation to the acknowledged prior art of Dunkin et al.

The structural component (B) is hydrophobic and/or lipophobic. The presence of this structural component causes a monomolecular film formed from the molecules to be in turn hydrophobic and/or lipophobic. Suitable examples of the structural component (B) are long chain hydrocarbons and long chain fluorinated carbon chains which may be perfluorinated or substituted by a mixture of fluorine and hydrogen atoms. Preferably such chains are saturated and/or branched, that is they may have a dendritic structure.

Examples of such chains include the saturated fluorinated chains —$(CH_2)_n(CF_2)_mCF_3$,—$(CH_2)_nCF[(CF_2)_mCF_3]_2$ and —$(CH_2)_nC[(CF_2)_mCF_3]_3$, (where n and m are integers, preferably 0 to 10 and 0 to 9, respectively.)

If the structural component (A) is an o-nitrobenzyl ester, then the structural component (B) can be easily introduced at the para-position of the benzyl group via an ether bond.

If the structural component (A) is an o-nitrobenzyl ester, then the molecule of the first aspect of the present invention preferably has a succinic imide structure as the terminal group of the benzyl group due to its advantageous reactivity. This succinic imide structure enables the resulting molecule to be easily coupled to a substrate which either has suitable surface reactive groups such as hydroxyl or amino groups, or may be coupled to such a substrate by means of a monolayer of a coupling compound (D) previously coated and/or bonded to the substrate which has a functional group reactive with the succinic imide structure such as a hydroxyl or amino group. This enables the molecules of the first aspect of the invention to be applied to practically any type of substrate such as the surface of a gold substrate which is surface-modified with amino groups, a surface of a semiconductor substrate such as silicon, an organic material surface of a plastics substrate or the surface of an insulating substrate. In this way, a photodegradable SAM can be produced.

For instance, a substrate such as a gold film may be coated with a monolayer of an aminosilane compound such as 3-aminopropyltrimethoxysilane which is then coupled to a molecule according to the first aspect of the present invention including an o-nitrobenzyl ester having a terminal succinic imide residue. Such a coupling mechanism enables the molecules of the first aspect of the present invention to be widely applied to many different types of substrate and so used in photo-patterning applications. The coupling compound (D) could have an alternative substituent reactive with a succinic imide residue such as a hydroxyl group.

Figure 2:
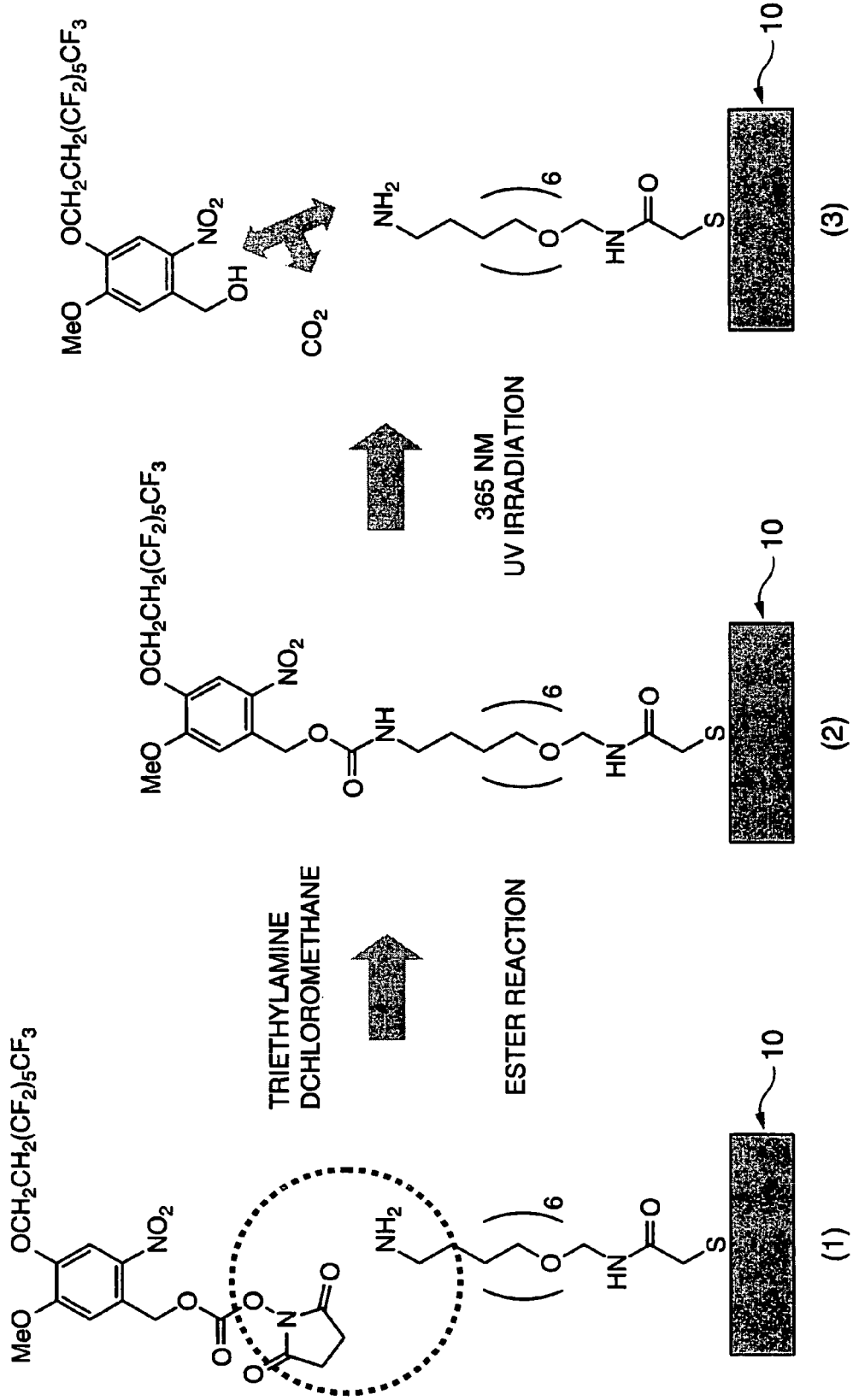
FIG. 2 shows the covalent bonding of a molecule according to the first aspect of the invention to a coupling compound (D) previously attached to a substrate and their subsequent cleavage when subjected to UV irradiation.

This coupling concept is more fully illustrated in FIGS. 2(1) and 2(2). In these Figures, a substrate (10) is initially treated with $HSCH_2CONHCH_2(OCH_2CH_2)_6\,CH_2CH_2NH_2$ as a coupling compound (D) which forms a monomolecular film (not illustrated) on the substrate (10). The film's surface includes reactive amino groups. These amino groups may then be reacted with molecules according to the first aspect of the present invention which bear a succinic imide residue at one terminal which reacts together with the amine substituent of the coupling compound (D) to form a carbamic ester structure. The reaction between the coupling compound and the molecule according to the first aspect of the present invention can be performed for example in an organic solvent such as dichloromethane using trimethylamine as a reaction catalyst. The substrate (10) may for instance be a metal substrate such as gold or silver since such metal substrates have relatively strong reactivity with thiols and disulphides. Therefore the coupling compounds readily react with the substrate to form a SAM on the substrate surface. An alternative coupling compound would be 11-aminododecanethiol.

The molecule of the first aspect of the present invention preferably has the general Formula (I):

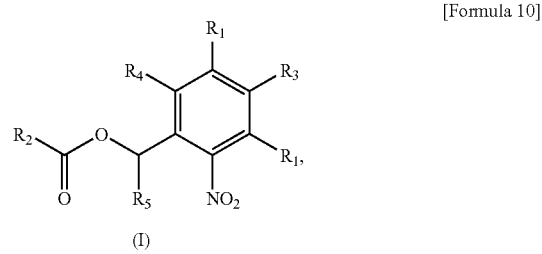

[Formula 10]

(I)

wherein, $R_1$ independently represents a hydrogen atom, —$OR_6$ ($R_6$ is an alkyl chain having a carbon number of 1 to 10), —$NH(CO)R_7$ ($R_7$ represents an alkyl chain having a carbon number of 1 to 10, or an alkyl fluoride chain having a carbon number of 1 to 10), $N(R_8)_2$ ($R_8$ represents an alkyl chain having a carbon number of 1 to 5) or —$S(R_9)$ ($R_9$ represents an alkyl chain having a carbon number of 1 to 10).

$R_2$ represents an N-hydroxy succinic imide group (optionally substituted with a sulfonyl group). $R_3$ represents —$X_2$—$(CH_2)_n$—$X_1$, wherein $X_2$ represents —$CH_2$— or —O—, n is 0 or an integer of 1 to 10, and $X_1$ represents —OZ, -Z or

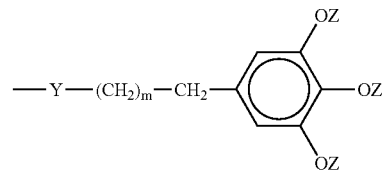

wherein, Y represents —$(CH_2)$— or —O—, Z represents a fluoroalkyl group having a carbon number of 1 to 20 and m represents 0 or an integer of 1 to 10; $R_4$ represents —$NO_2$ or a hydrogen atom; and $R_5$ is a hydrogen atom or an alkyl group having a carbon number of 1 to 10.

Such compounds are efficiently decomposed even when absorbing a small amount of UV radiation but enable a SAM to be formed having a high surface hydrophobic and/or lipophobic property.

It is particularly preferred in the above compounds of Formula (I) that the substituent $R_1$ should be a methoxy group (—$OCH_3$). This substitent is a structure in which a methoxy group is bonded to the para-position with respect to the nitro group. This substitution causes the compound to strongly absorb UV radiation in the wavelength range 330-360 nm. It is further preferred that $R_5$ is a hydrogen atom.

It is further preferred in the above compounds of general Formula (I) that the substituent Z is —$(CH_2)_m(CF_2)_pF$ or a branched chain isomer thereof wherein m is as defined above and p is 0 or an integer of 1 to 9.

If the molecules according to the aspect of the invention can be coated as a monolayer (a SAM) on a substrate having a hydrophilic surface, then the resulting monomolecular film coated substrate may be directly subjected to photo-patterning by exposure to UV irradiation. Thus UV irradiation will cleave the molecule at the structural component (A) exposing, after rinsing, the hydrophilic surface of the substrate. Areas of the monomolecular film which are masked from irradiation remain hydrophobic and/or lipophobic due to the structural component (B). As a consequence, such a coated substrate is able to demonstrate two different surface properties. Namely, there is a hydrophilic surface property in areas which have been subjected to UV irradiation and a hydrophobic and/or lipophobic surface property in other areas where they have not.

Alternatively, the molecules according to the aspect of the invention may be coupled to the surface of a substrate through a coupling compound (D) such as illustrated in FIG. 2(2). The resulting SAM has a carbamic ester structure. When the SAM surface is irradiated with UV radiation having a wavelength of for instance 365 nm through a photo-mask, photodecomposition of the SAM proceeds quite quickly, in about 30 seconds to 5 minutes, and the carbamic ester structure is decomposed. Subsequently, the film surface is rinsed with a suitable solvent such as water, and the original amino groups of the coupling compound (D) reappear on the film surface as illustrated in FIG. 2(3). As a consequence, a large difference exists in the surface energy between the UV irradiated regions of the SAM coated substrate and the non-irradiated regions.

In accordance with the above, a monomolecular film or SAM, is obtained whose wettability to a solution and solvent can be significantly altered by subjecting it to image-wise UV irradiation. For instance, when the above-described molecules containing a succinic imide residue are used, these molecules may be reacted with a hydroxy thiol, such as 11-hydroxydodecanethiol, by refluxing in acetonitrile as a solvent. This reaction produces a disulphide carbamate. Subsequently, this derivative may be fixed to a gold substrate to form a monomolecular film thereon. This coated substrate may then be irradiated with UV light having a wavelength in the range 254-400 nm in order to bring about a dissociation reaction. The reaction results in the cleavage away of the succinic imide derivative leaving only the 11-hydroxydodecanethiol, which presents hydroxyl groups on its film surface rendering the irradiated areas of the SAM hydrophilic. On the other hand, the unirradiated areas of the SAM remains hydrophobic and/or lipophobic due to the presence of the structural component (B).

As previously described, another aspect of the invention can provide a monomolecular film coated substrate. The film is formed from molecules including a structural component (B), which is hydrophobic and/or lipophobic, and a structural component (A), which decomposes when irradiated with UV light having a wavelength in the range 254-400 nm to cleave away a part of the molecule including the structural component (B) leaving a residual hydrophilic structural component (C).

The monomolecular film (SAM), which is deposited on the substrate will be understood to be a highly functional layer having two possible surface properties that is an initial hydrophobic and/or lipophobic property, and a hydrophilic property after being subjected to UV irradiation. These properties make such a monomolecular film coated substrate suitable for photo-patterning by UV irradiation. The structural component (A) and the structural component (B) are the same as described in respect of the first aspect of the present invention above. Accordingly, unless the monomolecular film of the second aspect of the present invention is particularly described in the following, the above description of the molecules of the first aspect of the present invention can be applied.

When turning to the residual hydrophilic structural component (C), the component is a hydrophilic substituent group such as an amine group or a hydroxyl group. This group is liberated upon cleavage of the structural component (A) caused by UV irradiation. This cleavage is particularly illustrated in FIGS. 2(2) and 2(3). According to this Figure, UV irradiation of the monomolecular film coated substrate of FIG. 2(2) causes cleavage of the o-nitrobenzyl ester structure. After rinsing away of the residues, the amine-substituted coupling compound (D) remains resulting in areas of the monomolecular film, which have been irradiated being hydrophilic. In contrast, areas masked from the UV irradiation will remain hydrophobic due to the chain-OCH$_2$CH$_2$(CF$_2$)$_5$CF$_3$ which constitutes the structural component (B).

The monomolecular film in the aspect of the invention is preferably obtainable by coating a substrate with a coupling compound (D), which comprises a hydrophilic moiety and subsequently reacting the hydrophilic moiety with a molecule according to the first aspect of the present invention. Alternatively, when the surface of the substrate is already hydrophilic, the monomolecular film coated substrate according to the second aspect of the present invention may be obtained simply by coating onto the substrate molecules according to the aspect of the invention to form a SAM.

Once the monomolecular film coated substrate has been subjected to photo-patterning, then for instance a polymer solution containing a functional material may be applied to its surface by conventional techniques such as spin coating or ink jet printing which selectively applies the solution. The functional material will be deposited over the patterned monomolecular film which in turn allows the functional material to be easily patterned.

As described above, the invention can provide in another aspect a method of photo-patterning a monomolecular film coated substrate as described above. The method can include the step of image-wise irradiating the monomolecular film coated substrate with UV light having a wavelength in the range 254-400 nm through a patterned mask to cleave the coated molecules at the structural component (A) thus removing the structural component (B) from the coated film in the irradiated areas converting them from being hydrophobic and/or lipophobic to hydrophilic.

Techniques of photo-patterning using light irradiation and masks are well known to those working in the field of resist technology.

It will be appreciated that the method according to the aspect of the invention allows photo-patterning to take place requiring only a monomolecular film coating on a substrate. The method therefore solves the problem of substantial wastage referred to in the introduction of this specification when using conventional photosensitive polymer materials applied by spin coating. In addition, the two-stage method of forming a monomolecular film provided by the invention which includes designing and synthesizing molecules in accordance with the first aspect of the present invention having both a UV degradable structure and a hydrophobic and/or lipophobic structural component and then coupling these two structures to a coupling compound (D) via a hydrophilic moiety on the former. The two-stage method provides a widely applicable technique for photo-patterning a variety of substrate types.

The compound (the compound (0)) of the aspect of the invention is presented as following Formula (0).

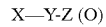

[Formula 11]

The end of it is provided with the structure X having reactivity with functional group on the solid-phase surface. For example, when a glass substrate is used as the solid-phase substrate, the surface of the substrate has aplenty of hydroxyl group. X can be, for example, alkoxy silane or silane halide-SiL (where L represents alkoxy group or halide and n represents an integer number of 1 to 4). L part is decomposed by water thereby and coupled to hydroxyl group resulting in the compound (0) fixed onto the solid-phase surface.

X is appropriately selected from solid-phase materials and compounds fixed onto the surface except the above alkoxy silane or silane halide. X is not specifically limited so long as having reactivity with functional group with a solid-phase surface. But, it is preferably selected from high reactive structures such as any of groups including amino group, urethane group, carboxyl group, carbonyl group, urea group, sulfonic group, disulfide group, epoxy group, carbodiimide group, maleimido group, alkoxy silane, silane halide, and N-hydroxy succinic imide group.

According to another aspect of the invention, droplets including the above compound (0) is ejected onto the solid-phase surface having a functional group. Here, the functional group possessed by the solid surface may be a functional group owned by the solid phase material itself or a functional group owned by a compound which is fixed onto the solid surface in advance. When the solid phase surface is a glass substrate described above, a hydroxyl group possessed by the glass substrate can be used as a functional group of the solid surface. Further, when the solid-phase material has not a functional group to be coupled with X, a compound having a functional group to be coupled with X is fixed onto the solid-phase surface in advance prior to ejecting droplets including the compound (0).

The functional group possessed by the solid-phase surface is preferably selected from any of groups including amino group, urethane group, carboxyl group, carbonyl group, urea group, sulfonic group, thiol group, sulfide group, disulfide group, epoxy group, carbodiimide group, maleimido group, alkoxy silane, silane halide, and N-hydroxy succinic imide (NHS) group.

A method of fixing a compound having these functional groups is not specifically limited. But, the end opposite to these functional groups, for example, can be coupled with a functional group for forming SAM corresponding to a solid-phase material such as the above —SiLn, for example, (where L represents alkoxy group or halide and n represents an integer number of 1 to 4) thiol group, sulfide group, disulfide group, and others. SAM can be formed thereby and contacting a solution including the compound with the solid-phase surface and fixed.

The compound (0) is provided with the structure Z, which can change solid-state property of the solid-phase surface or reactive property at the end opposite to X.

The solid-state property of the solid phase surface can be, for instance, response to wettability, heat and pressure, configuration, viscosity, adhesion, water absorption, elasticity and others. Particularly, a structure having wettability is preferable for Z.

Controlling wettability such as hydrophobicity, hydrophilicity, lipophobicity and lipophilicity enables materials to be fixed to appropriately be absorbed onto a region desired for fixing of the solid phase surface. On the other hand, fixing them onto other regions can be prevented. The structures controlling favorable wettability as Z are, for example, the following: as the structure giving hydrophobicity to the solid-phase surface, a saturated or unsaturated alkyl chain optionally having a substituent, and a saturated or unsaturated fluorinated chain optionally having a substituent are cited. As the structure giving hydrophilicity to the solid-phase surface, hydoxyl group and amino group are cited.

Meanwhile, the favorite reactive structure as Z is a functional group having high reactivity. The group is, for example, selected from hydoxyl group, amino group, urethane group, carboxyl group, carbonyl group, urea group, sulfonic group, disulfide group, epoxy group, carbodiimide group, maleimido group, N-hydroxy succinic imide group. Further, Z can be diluted into appropriate solvents, which are specifically not limited so long as ejected as droplets. These are molecules such as avidin, biotin, antigen, antibody and protein A having biological affinity.

The compound (0) used in an aspect of the invention can be located between X and Z, and possesses the structure Y which is decomposable by itself. The decomposability of Y allows Z to be cleaved away from the solid-phase surface by decomposing Y after fixing the compound (0). This process enables solid-state property and reactive property that have been given by Z once, to be returned to the original states. Further, the decomposition of Y enables the solid-phase surface to receive new solid-state property and reactivity by newly exposed atoms.

A method of decomposition is not specifically limited. But, this can be attained as followings. A solution including a compound having property, which decomposes Y, is contacted with the solid-phase surface. Or a solution including such compound is applied to the solid-phase surface by the micro droplet ejecting means.

Y is preferably a structure having optical response. Irradiating light onto the solid phase surface easily decomposes Y thereby. Further, when using an appropriate mask, Y can be decomposed only in a part of area where the compound (0) is fixed.

The following Formula (I) is cited as a preferable embodiment for the above compound (0):

[Formula 12]

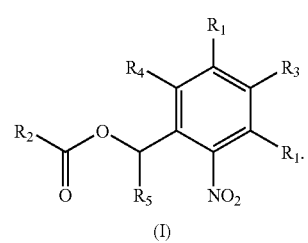

(I)

wherein, $R_1$ independently represents a hydrogen atom, —$OR_6$ ($R_6$ is an alkyl chain having a carbon number of 1 to 10), —$NH(CO)R_7$ ($R_7$ represents an alkyl chain having a carbon number of 1 to 10, or an alkyl fluoride chain having a carbon number of 1 to 10), $N(R_8)_2$ ($R_8$ represents an alkyl chain having a carbon number of 1 to 5) or —$S(R_9)$ ($R_9$ represents an alkyl chain having a carbon number of 1 to 10). $R_2$ represents an N-hydroxy succinic imide group (optionally substituted with a sulfonyl group). $R_3$ represents —$X_2$—$(CH_2)_n$—$X_1$, wherein $X_2$ represents —$CH_2$— or —O—, n is 0 or an integer of 1 to 10, and $X_1$ represents —OZ, -Z or

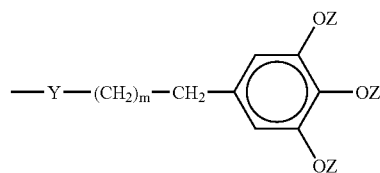

wherein, Y represents —($CH_2$)— or —O—, Z represents a fluoroalkyl group having a carbon number of 1 to 20 and m represents 0 or an integer of 1 to 10. R4 represents —$NO_2$ or a hydrogen atom; and $R_5$ is a hydrogen atom or an alkyl group having a carbon number of 1 to 10.

In this compound, R2 which is a NHS residual group, or a NHS residual group having a sulfonyl group, functions as the structure X and the compound (I) is easily fixed onto the solid-phase surface if an amino group exists as a functional group on the solid-phase surface. R3 including fluorite chain functions as the structure Z and changes the solid-state property of the solid-phase surface to hydrophobic and/or liophobic.

Figure 4:
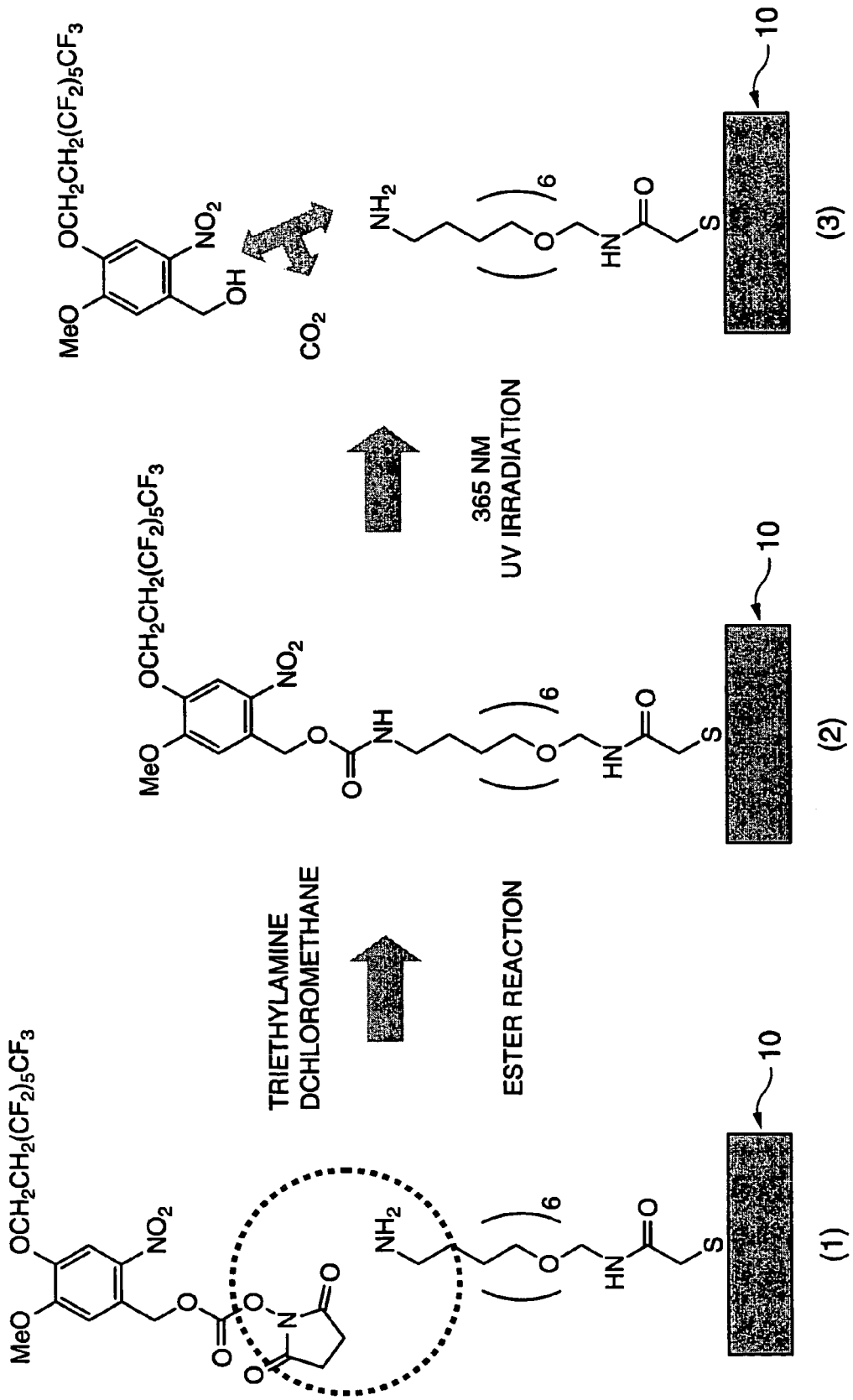
FIG. 4 shows explanation of an optical response of a compound used in the fourth aspect of the invention.

Further, the compound is decomposed absorbing ultra violet ray of long wavelength such as 254 nm to 400 nm preferably by the reaction shown in FIG. 4.

Therefore, the compound (I) is fixed onto the solid-phase surface (10) once giving hydrophobic and/or liophobic property to the solid phase surface. Then, irradiating ultra violet lay removes the structure Z including fluorite chain from the solid-phase surface changing the solid-state property of the surface to be hydrophilic again.

The compounds represented by the following Formula (II) and (III) are cited as the compound represented by the above Formula (I).

Further, in the method of an aspect of the invention, a device for controlling drying droplets is preferably applied when ejecting droplets. It is easy to dry droplets ejected by a micro droplet ejecting means because of a small amount of volume. Hence, in order to assure sufficient time for reacting the structure X with a functional group on the solid-phase surface, it is preferable to extend time for drying droplets. As the means of means for controlling drying droplets, a device for shortening a distance between droplets, a means for ejecting droplets (a solvent or solution) again prior to drying droplets, a means for adding a coating material and a means for delaying moving speed of a stage where a solid-phase is installed in case of an inkjet method are cited as examples.

The following exemplary embodiments provide further details of the present invention. However, it should be noted that the present invention is in no way limited to the specifics of these embodiments. As would be obvious to one skilled in the art, many variations and modifications to the embodiment can be made without departing from the spirit and scope of the invention, and they fall within the scope of the appended claims.

[Formula 13]

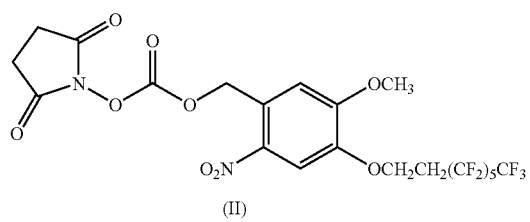

(II)

[Formula 14]

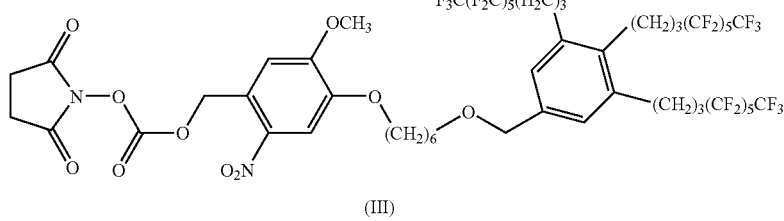

(III)

A micropipette, a micro dispenser and an ink jet method are cited as a method ejecting droplets used in the fourth aspect of the present invention. Particularly, an inkjet method is preferable for precise patterning. The ink jetting employs various ways for ejecting liquid, including piezo jet using piezo elements, thermal jet using thermal elements, and electrostatic actuation utilizing electrostatic forces between an oscillating plate and an electrode. Preferably, the piezo jet and electrostatic actuation, which have no effect of high temperature on ejected liquid, may be used with temperature-sensitive biological substances.

The solvent for the compound (I) used in the fourth aspect of the invention is not specifically limited if it is a liquid, which is capable of being ejected by a micro droplet ejecting means. But, it is preferably a solvent or a compound, which has high solubility to the compound (I) and low saturated vapor pressure, namely low boiling point and uneasy to dry. As the solvent, for example, DMF, DMSO, HNPA, a pyrrolidone group solvent, and a proton polar solvent such as dioxane are cited.

Synthesis of the Following Compound 1

[Formula 15]

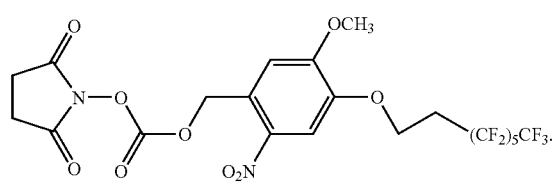

The compound 1 was prepared in accordance with the synthesis set out in FIG. 1 and its reaction steps 1-4.

The spectral data of 1H nmR, $^{13}$C nmR, MS, and the like for the material (white solid) synthesized in reaction step (1) are as follows, and this material was identified as 4-(1H, 1H, 2H, 2H-perfluorooctyloxy)-3-methoxy-benzaldehyde (a yield of 30%).

$^1$H nmR (300 MHz, CDCl3) 9.87 (s, 1H, Ar—H), 7.48-7.43 (m, 2H, Ar—H), 6.99 (d, 1H, Ar—H), 4.43-4.38 (t, 2H), 3.93 (s, 3H), 2.81-2.69 (m, 2H); $^{13}$C nmR (75 MHz, CDCl3) 191.28, 153.26, 150.35, 131.28, 126.90, 1112.34, 110.02, 61.54, 56.47, 31.82, 31.54, 31.25; MS (ES+) 499 ([M+H]$^+$, 55), 454 (20), 391 9220, 279 (5), 241 (5).

The spectral data of 1H nmR, 1 $^{13}$C nmR, MS, elemental analysis, and the like for the material (yellow solid) synthesized in reaction step (2) are as follows, and this material was identified as 2-nitro-4-(1H, 1H, 2H, 2H-perfluorooctyloxy)-5-methoxy-benzaldehyde (a yield of 80%).

$^1$H nmR (300 MHz, CDCl$_3$) 7.64 (s, 1H, Ar—H), 7.43 (s, 1H, Ar—H), 4.47-4.43 (t, 2H), 4.01 (s, 3H), 2.86-2.69 (m, 2H); $^{13}$C nmR (75 MHz, CDCl3) 188.08, 154.01, 151.17, 126.77, 110.71, 108.91, 91.23, 62.28, 57.17, 31.78, 31.48, 31.21; MS (ES+) 544 ([M+H]$^+$, 100), 514 (15), 410 (15), 282 (10), 178 (10); Anal. Calcd. for C$_1$ 6H$_{10}$F$_{13}$O$_5$N: C, 35.35%; H, 1.85%; N, 2.57% found C, 35.35%; H, 1.95%; N, 2.75%.

The spectral data of 1H nmR and 1$^{3}$C nmR for the material (solid) synthesized in reaction step (3) are as follows, and this material was identified as 2-nitro-4-(1H, 1H, 2H, 2H-perfluorooctyloxy)-5-methoxy-benzyl alcohol (a yield of 70%).

1H nmR (300 MHz, CDCl3) 7.74 (s, 1H, Ar—H), 7.22 (s, 1H, Ar—H), 4.98 (s, 2H), 4.40-4.35 (t, 2H), 3.99 (s, 3H), 2.82-2.65 (m, 2H), 2.62 (br.s, 1H); $^{13}$C nmR (75 MHz, CDCl$_3$) 154.80, 146.79, 139.89, 133.75, 111.82, 110.56, 63.18, 56.90, 31.80, 31.54, 31.26.

The spectral data of 1H nmR, 1$^{3}$C nmR, MS, elemental analysis, and the like for the material (pale yellow solid) synthesized in reaction step (4) are as follows, and this material was identified as the compound 1 (a yield of 62%).

$^1$H nmR (300 MHz, CDCl$_3$) 7.80 (s, 1H, Ar—H), 7.23 (s, 1H, Ar—H), 5.99 (s, 2H), 4.41-4.37 (t, 2H), 4.05 (s, 3H), 2.87 (s, 4H), 2.80-2.68 (m, 2H); $^{13}$C nmR (75 MHz, CDCl$_3$) 168.88, 155.07, 151.81, 147.36, 139.23, 126.89, 110.54, 109.49, 69.48, 62.09, 57.08, 31.76, 31.51, 31.23, 25.86; MS(FAB) 686 ([M]$^+$, 8), 528 (100); HRMS (ES+) Calcd. For C$_{21}$H$_{15}$N$_2$O$_9$F$_{13}$Na 709.0468, found 709.0473; Anal. Calcd. For C$_{21}$H 1$_5$N$_2$O$_9$F$_{13}$: C, 36.73%; H, 2.20%; N 4.08% found C, 36.45%; H 2.35%; N 4.25%.

A gold film was formed on a surface of a silicon substrate by sputtering. Separately, a thiol solution was prepared by dissolving 1 mm of 11-aminodecanethiol in ethanol. Next, the substrate provided with the gold film thereon was immersed into the thiol solution at room temperature for 12 hours. The substrate was then rinsed with ethanol and subsequently dried under nitrogen flow. This resulted in a SAM film of 11-aminodecanethiol being formed on the gold surface of the substrate.

Subsequently, 150 mg of the compound 1 as synthesized and purified in Embodiment 1 was dissolved in 100 ml of anhydrous dichloromethane to form a solution at a concentration of approximately 2 mM, and 2 ml of triethylamine was dissolved in the solution thus formed, thereby preparing a solution of compound 1. Next, the above-described substrate (hereinafter referred to as the "amino-surface substrate") having amino functional groups on the surface thereof was immersed in the solution thus prepared at room temperature for half a day, which allows the reaction between the succinic imide ester of compound 1 and the amino group of the amino-surface substrate to proceed. This reaction is illustrated in FIGS. 2(1) and 2(2). After this reaction, the substrate was rinsed with dichloromethane, followed by drying by flowing nitrogen gas. A fluorinated chain modified SAM composed of molecules each having the structure shown in FIG. 2(2) was thus formed on the substrate surface.

The contact angle of the SAM (monomolecular film) surface thus formed was measured, and the advance angle (water) was approximately 90 to 100°. The variation in the measured angle is believed to be due to variations in the molecular coating state of the fluorinated chain modified SAM.

Figure 3:
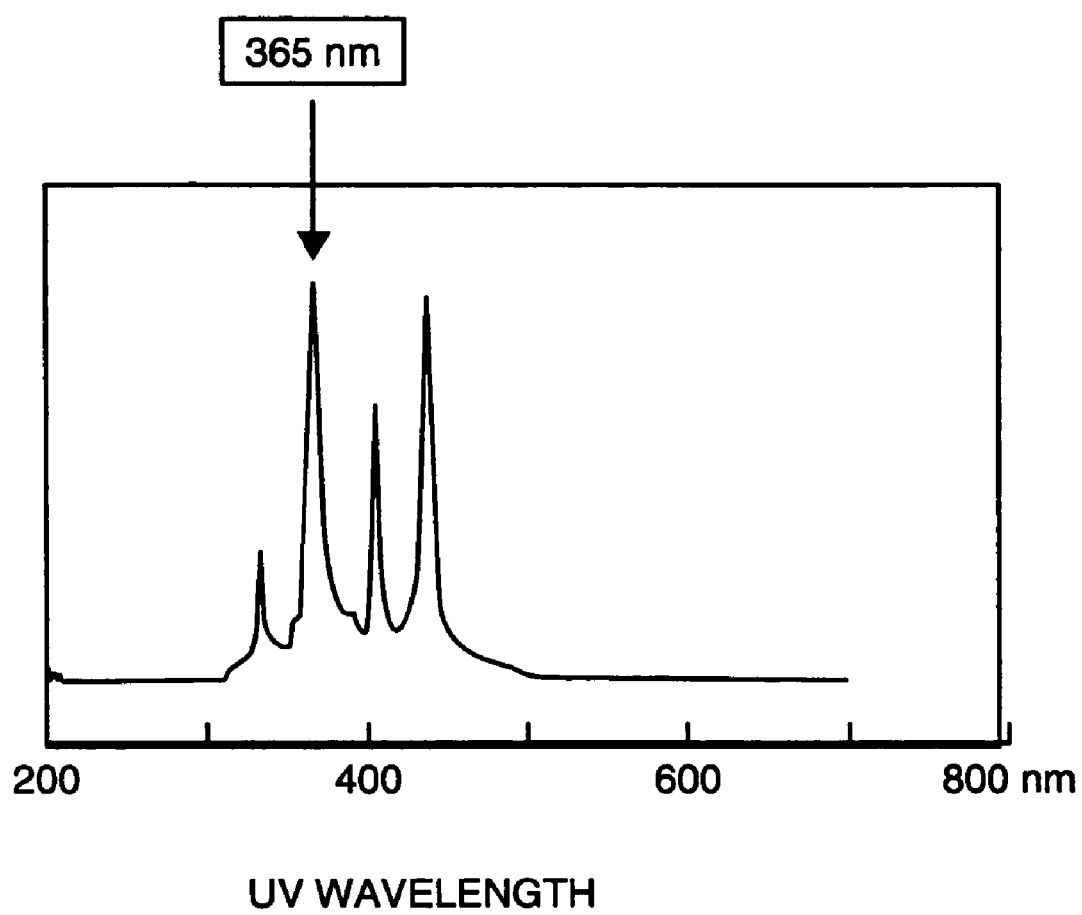
FIG. 3 shows the UV irradiation energy distribution which can be used to expose a monomolecular film coated substrate in accordance with the second aspect of the invention.

The fluorinated chain modified SAM surface was then irradiated with UV having a wavelength of 365 nm through a photomask for varying time periods (1 minute, 5 minutes, 10 minutes, etc.). The UV irradiation energy distribution used is illustrated in FIG. 3. The UV irradiation energy was approximately 30 mW/cm$^2$. The UV irradiation resulted in the decomposition reaction shown in FIGS. 2(2) and 2(3) to occur, and as a result, a SAM having amino groups represented by the structure shown in FIG. 2(3) was formed on the surface by decomposition.

After the UV irradiation, the substrate surface was rinsed with ethanol, and the change in the surface contact angle (advance angle (water)) at four different locations where the SAM had been irradiated was measured. The results of the measurement are listed in Table 1. The followings are clarified by the result shown in Table 1. The contact angle is reduced to approximately 50° when the SAM is irradiated for 1 to 5 minutes suggesting that the decomposition of the coupled SAM is substantially completed during this time period. Since the contact angle of the SAM surface when covered only with 11-aminodecanethiol was measured to be approximately 43°, it is believed that most of the fluorinated chains were removed by the irradiation.

In addition, the SAM was immersed in water after the irradiation and rinsing steps and was then pulled out therefrom. The surface of the SAM was then immediately observed. Water droplets were observed to remain where the SAM surface had been irradiated with UV that is the hydrophilic property was confirmed. On the other hand, the SAM surface repelled water at locations where it had been masked from the TV radiation that is the hydrophobic property was maintained.

The silicon substrate coated with a solid film used as a starting substrate in exemplary embodiment 2 was immersed in a dichloromethane solution containing 1 mm of HS(CH$_2$)$_2$(CF$_2$)$_9$CF$_3$. Then UV irradiation was performed in a manner similar to that in Embodiment 2, and the wettability of the surface was analyzed. As a result, the contact angle before UV treatment was 110° with respect to water, and the contact angle after UV irradiation for 5 minutes was approximately 109°, that is essentially unchanged. Accordingly, it was confirmed that a SAM formed from HS(CH$_2$)$_2$(CF$_2$)$_9$ was hardly decomposed by UV light (see the right-hand column of Table 1).

TABLE 1

| Area Measured | Exemplary Embodiment 2 Compound 1 | | | | Comparative Example |
| --- | --- | --- | --- | --- | --- |
| | 1 C.A(°) | 2 C.A(°) | 3 C.A(°) | 4 C.A(°) | CF$_3$(CF$_2$)$_9$(CH$_2$)$_2$SH C.A(°) |
| UV 0 min | 95 | 97 | 102 | 98 | 110 |
| UV 1 min | 67 | 67.8 | 66 | 69 | 109 |
| UV 5 min | 53.1 | 53 | 52.6 | 53.1 | 109 |
| UV 10 min | 50 | 49.5 | 49.7 | 50.9 | 108 |
| UV 20 min | 50.5 | 50.1 | 50.8 | 51.4 | 104 |
| UV 30 min | 48.5 | 49.7 | 48.8 | 48.9 | 105 |
| UV 60 min | 49.2 | 49.7 | 50.1 | 51.1 | 103 |

From the above description, it can be understood that the invention provides a self-assembled monolayer (SAM) material which can form a monomolecular film on a substrate and which can be photo-patterned by a relatively short exposure to low energy UV irradiation. The SAM material provided can be applied to a variety of different types of substrates by means of suitable coupling compounds. Prior to irradiation, the SAM material is hydrophobic and/or lipophobic. Irradiation however cleaves away the structural component responsible for this property leaving behind a functional group which is hydrophilic. Irradiation of the SAM material therefore substantially alters the surface property of the SAM-coated substrate.

In the embodiment, wettability of the solid-phase surface is controlled by ejecting solution of the compound described as the above Formula (II) (called as the compound (II)). The compound (II) includes a N-hydroxy succinic imide group as the structure X, a structure having photic-decomposable property as the structure Y, a fluorinated chain as the structure Z, which changes the solid-state property of the solid-phase surface to hydrophobic and/or lipophobic.

Preprocessing the Surface of the Substrate

Figure 5:
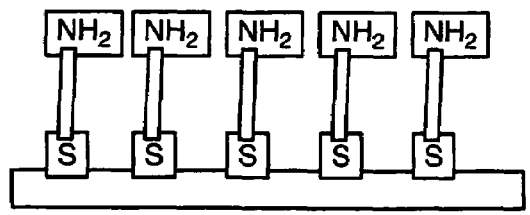
FIG. 5 is a diagram showing fixing an amino group onto the solid-phase surface.

First, as shown in FIG. 5, 11-amino dodecanethiol is fixed to the substrate surface. This compound is capable of coupling with a N-hydroxy succinic imide of the compound (II). The substrate is silicon and coated with a gold film by evaporation in advance. The gold film is also formed by sputtering.

11-amino dodecanethiol is dissolved into ethanol to be 1 mM and the substrate is immersed into this solution. The substrate was then rinsed with ethanol and subsequently dried under nitrogen flow. The substrate surface is covered with an amino group and turned to be hydrophilic.

Fixing the Compound (II)

Next, 150 mg of the compound I is dissolved into 100 mL of anhydrous DMSO (dimethyl sulfoxide) to be about 2 mM solution and 2 mL of trimethyl amine is added.

Figure 6:
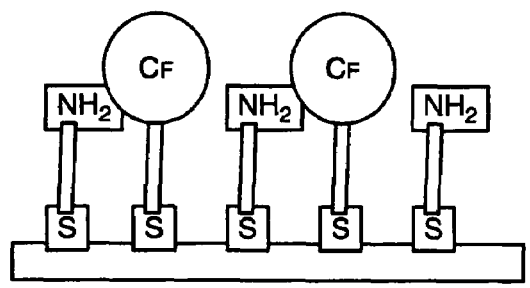
FIG. 6 is a diagram showing fixing a compound (II) onto an amino group of the solid-phase surface.
Figure 7:
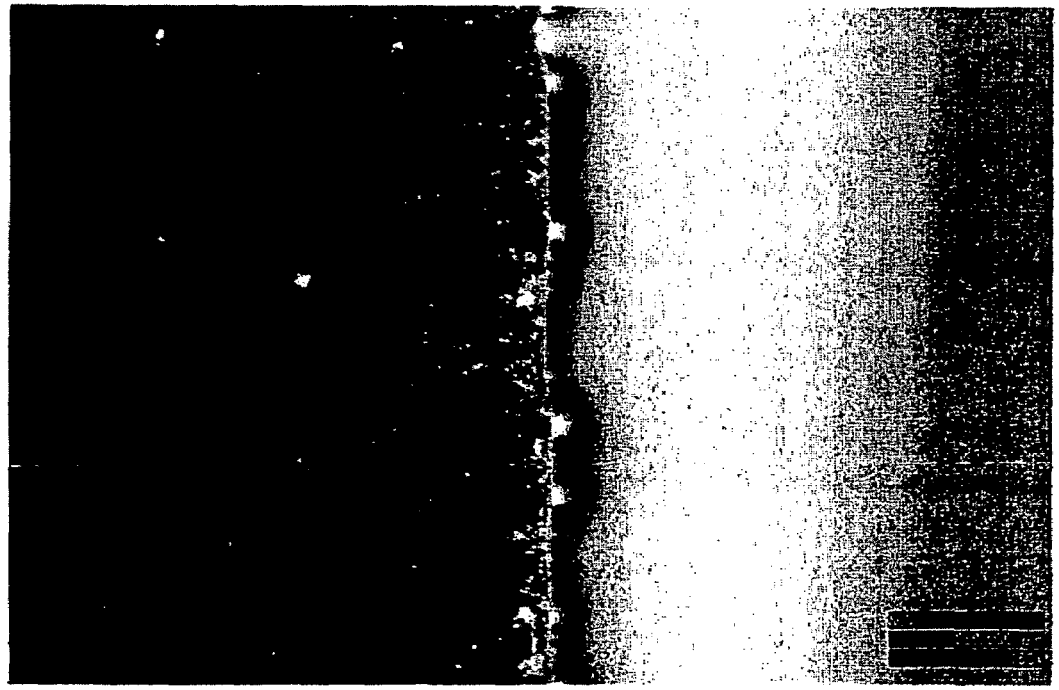
FIG. 7 is diagram showing observed water-shedding property of the compound (II)
Figure 8:
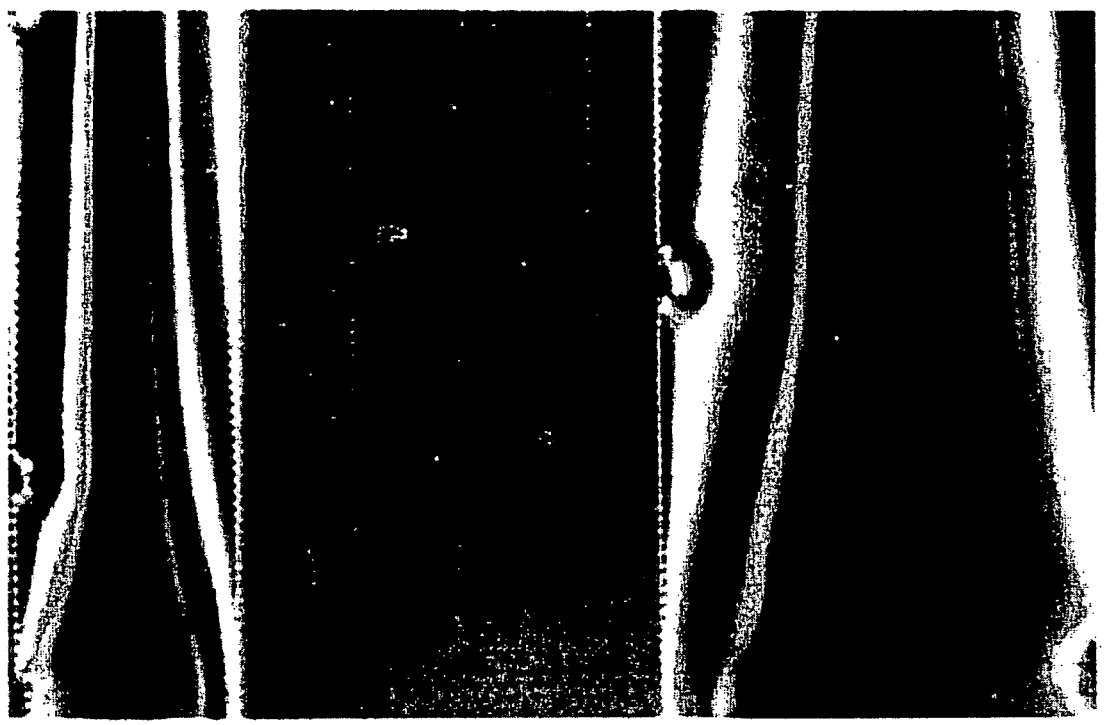
FIG. 8 is diagram showing observed water-shedding property of the compound (II)
Figure 9:
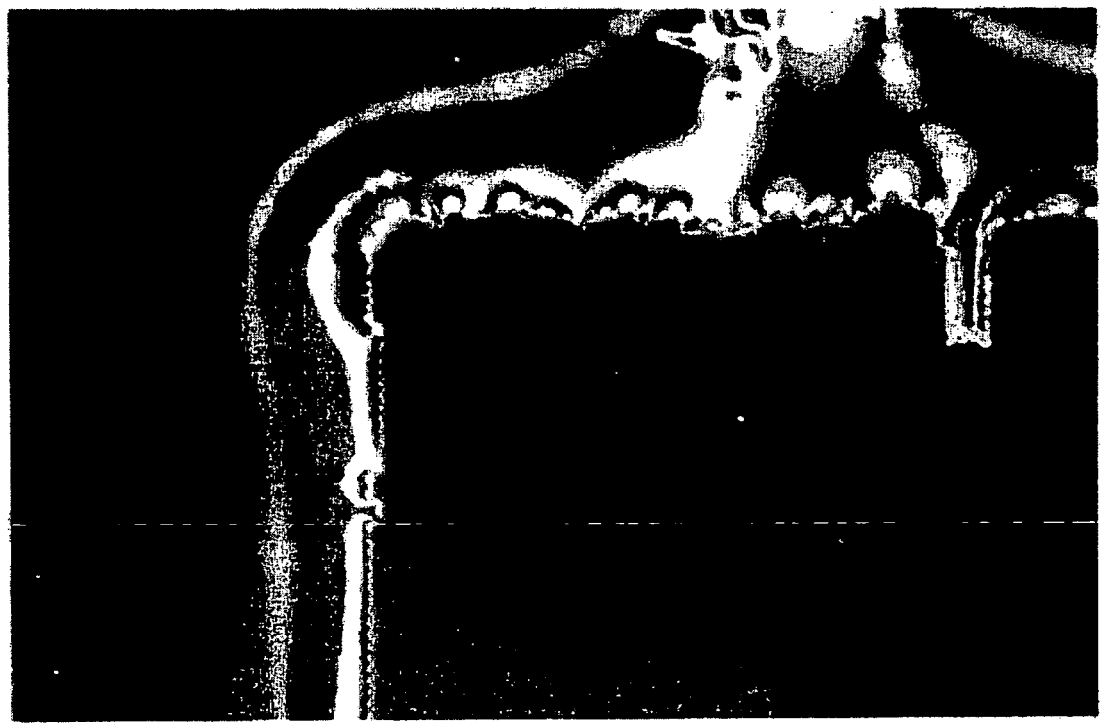
FIG. 9 is diagram showing observed water-shedding property of the compound (II)
Figure 10:
FIG. 10 is diagram showing observed water-shedding property of the compound (II)

As shown in FIG. 6, after deaerating solution, the solution is flown into an ink reservoir of ink-jet type ejecting device and ejected on the given location of the above amino substrate surface.

After this ejection, the substrate was rinsed with DMSO, followed by drying by flowing nitrogen gas. As the result, the compound (II) is fixed only onto a region where droplets are ejected and hydrophobic and/or liophobic property is given by fluorinated chain represented as CF. On the other hand, a region where droplets are not ejected shows hydrophilic since the amino group remains exposed.

Water is developed onto the surface and observed by a microscope. The observed results are shown in FIG. 7 to FIG. 10. According to FIGS. 7 and 8, it is confirmed that water is shed in the region where the solution of the compound (II) is ejected. Further, in FIG. 9 and FIG. 10, it is confirmed that a polar organic solvent such as ethanol is also shed showing printed pattern and the region where the solution of the compound (II) is ejected and a liquid is not attached to the substrate surface.

Fixing the Amino Protective Group

Figure 11:
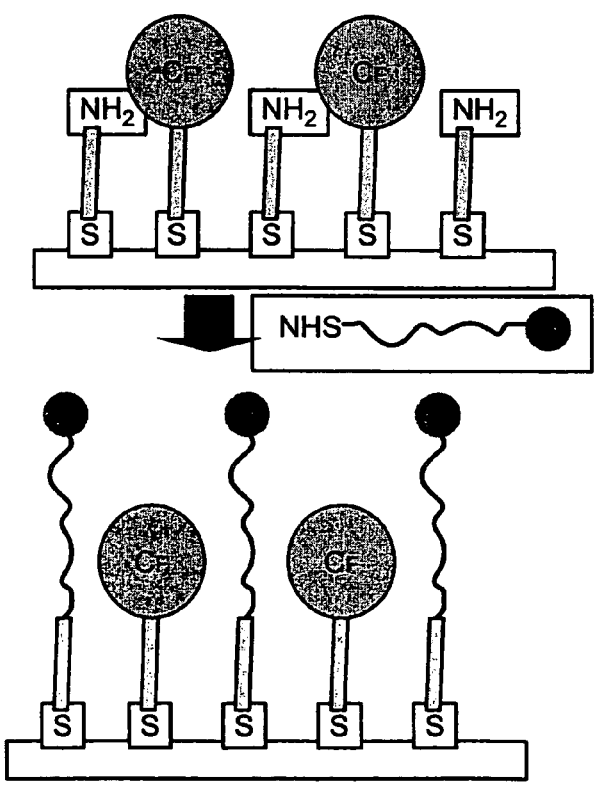
FIG. 11 is a diagram showing fixing an amino protective group onto an amino group of the solid-phase surface.

Next, as shown in FIG. 11, DMSO solution such as 9-Fluoprenylmethyl succinimidyl carbonate, for example, is ejected by the ink jet method or the like in the region where the compound (II) is not ejected. Otherwise, the substrate where the compound (II) is patterned is immersed into the solution so that an amino protective group is reacted and fixed. As the amino protective group, benzyl N-succinimidyl carbonate, di-tert-butyldicarbamate and N-Boc imidasole are also cited.

Decomposing the Compound (II)

Figure 12:
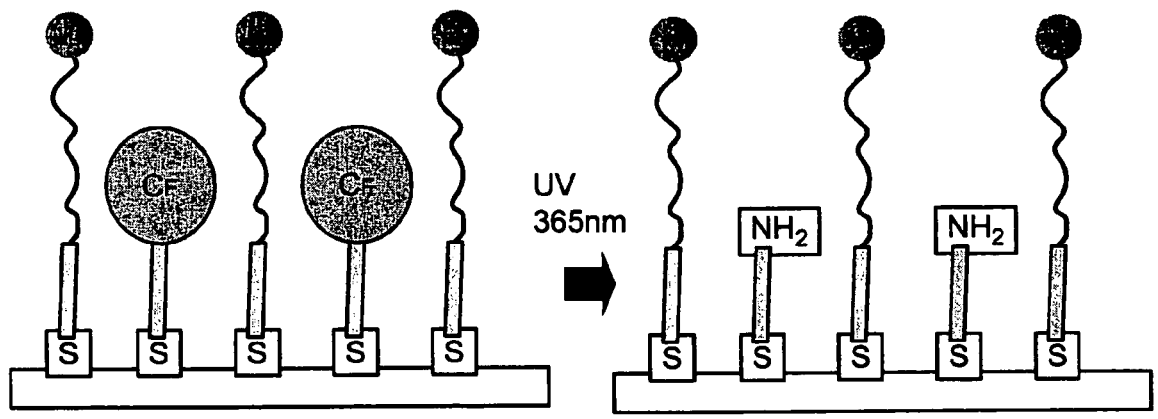
FIG. 12 is a diagram showing decomposing a compound (II) by irradiating UV onto the solid-phase surface.

Subsequently, as shown in FIG. 12, 308 nm UV is irradiated onto the substrate surface. The compound (II) is dissolved thereby with reaction shown in FIG. 4 and fluorinated chain represented as CF is removed from the substrate surface exposing an amino group again and showing hydrophilic property in this region. Then, the active amino group is reacted with a solution where NHS ester (NHS-LC-LC-Biotin, a reagent produced by Pierce Inc.) is dissolved forming a micro pattern covered with the biotin. Further, on this pattern, HRP(horseladish peroxidase) enzyme molecule conjugated with streptavidin is fixed for example, easily forming a micro pattern of an enzyme monomolecular film.

What is claimed is:

1. A molecule, comprising:
   a structural component (A) which decomposes when irradiated with UV light having a wavelength in the range 254-400 nm;
   a structural component (B) which is at least one of hydrophobic and lipophobic;
   the structural component (A) being an o-nitrobenzyl ester; and
   a terminal group bonded to the benzyl group of the o-nitrobenzyl ester being a succinic imide.

2. The molecule according to claim 1,
   the structural component (B) further comprising a fluorinated chain.

3. The molecule according to claim 2,
   the fluorinated chain being saturated.

4. The molecule according to claim 2, the fluorinated chain being at least one of branched and perfluorinated.

5. The molecule according to claim 1, further including having the following general Formula (1):

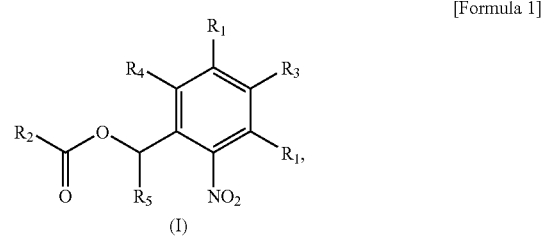

[Formula 1]

(I)

wherein:

$R_1$ independently represents a hydrogen atom, $-OR_6$ ($R_6$ is an alkyl chain having a carbon number of 1 to 10), $-NH(CO)R_7$ ($R_7$ represents an alkyl chain having a carbon number of 1 to 10, or an alkyl fluoride chain having a carbon number of 1 to 10), $N(R_8)_2$ ($R_8$ represents an alkyl chain having a carbon number of 1 to 5) or $-S(R_9)$ ($R_9$ represents an alkyl chain having a carbon number of 1 to 10);

$R_2$ represents an N-hydroxy succinic imide group (optionally substituted with a sulfonyl group);

$R_3$ represents $-X_2-(CH_2)_n-X_1$, wherein $X_2$ represents $-CH_2-$ or $-O-$, n is 0 or an integer of 1 to 10, and $X_1$ represents $-OZ$, -Z or

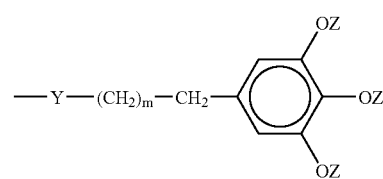

wherein:

Y represents —(CH$_2$)— or —O—, Z represents a fluoroalkyl group having a carbon number of 1 to 20 and m represents 0 or an integer of 1 to 10;

R$_4$ represents —NO$_2$ or a hydrogen atom; and

R$_5$ is a hydrogen atom or an alkyl group having a carbon number of 1 to 10.

6. The molecule according to claim 5, R$_1$ being —OCH$_3$.

7. The molecule according to claim 5, Z being —(CH$_2$)$_m$(CF$_2$)$_p$F or a branched chain isomer thereof, wherein m is as defined above and p is 0 or an integer of 1 to 9.

8. The molecule according to claim 1, which is the following compound:

[Formula 2]

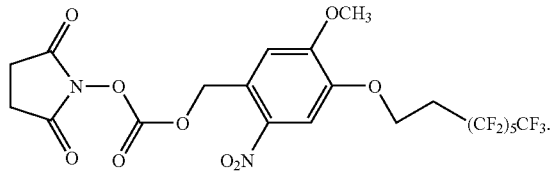

9. A monomolecular film coated substrate, the film being formed from molecules comprising:

a structural component (B) which is at least one of hydrophobic and lipophobic;

a structural component (A) which decomposes when irradiated with UV light having a wavelength in the range 254-400 nm to cleave away a part of the molecule comprising the structural component (B) leaving a residual hydrophilic structural component (C);

the structural component (A) being an o-nitrobenzyl ester; and the structural component (B) further including a fluorinated chain.

10. The monomolecular film coated substrate according to claim 9, the fluorinated chain being saturated.

11. The monomolecular film coated substrate according to claim 9, the fluorinated chain being at least one of branched and perfluorinated.

12. The monomolecular film coated substrate according to claim 9, the hydrophilic structural component (C) including an amine group or a hydroxyl group.

13. The monomolecular film coated substrate according to claim 9 obtainable by coating a substrate with a monomolecular film of a coupling compound (D) which comprises a hydrophilic moiety, and subsequently reacting the hydrophilic moiety with a molecule including a structural component (A) which decomposes when irradiated with UV light having a wavelength in the range 254-400 nm, and a structural component (B) which is at least one of hydrophobic and lipophobic, to covalently bond the coupling compound (D) and the molecule.

14. The monomolecular film coated substrate according to claim 13, the substrate being formed from at least one of a metal, a semiconductor and a plastic.

15. The monomolecular film coated substrate according to claim 13, the hydrophilic moiety being an amine group or a hydroxyl group.

16. The monomolecular film coated substrate according to claim 9, the molecules forming the film being molecules including a structural component (A) which decomposes when irradiated with UV light having a wavelength in the range 254-400 nm, and a structural component (B) which is at least one of hydrophobic and lipophobic.

17. The monomolecular film coated substrate according to claim 9, the substrate having a hydrophilic surface prior to coating with the monomolecular film.

18. The method of photo-patterning the monomolecular film coated on a substrate as defined in claim 9, comprising:

the step of image-wise irradiating the monomolecular film coated substrate with UV light having a wavelength in the range 254-400 nm through a patterned mask to cleave the coated molecules at the structural component (A), thus removing the structural component (B) from the coated film in the irradiated areas converting them from being at least one of hydrophobic and liophobic to hydrophilic.

19. A method of forming a film pattern, comprising at least a step of ejecting a droplet, which includes a compound represented as the following Formula (0), on a solid-phase surface having a functional moiety;

X—Y-Z (0)

where, X represents a structural component having reactivity with a functional moiety which exists at the solid-phase surface, Y represents a decomposable structural component by itself, and Z represents a structural component which is capable of changing a solid-state property on the solid-phase surface or a reactive structural component.

20. The method according to claim 19, the solid-state property being wettablity.

21. The method according to claim 19,

Z including a structural component, which is selected from any of groups including a saturated or unsaturated alkyl chain optionally having a substituent, a saturated or unsaturated fluorinated chain optionally having a substituent, hydoxyl group, amino group, urethane group, carboxyl group, carbonyl group, urea group, sulfonic group, disulfide group, epoxy group, carbodiimide group, maleimido group, and N-hydroxy succinic imide group.

22. The method according to claim 19,

X including a structural component, which is selected from any of groups including amino group, urethane group, carboxyl group, carbonyl group, urea group, sulfonic group, disulfide group, epoxy group, carbodiimide group, maleimido group, alkoxy silane, silane halide, and N-hydroxy succinic imide group.

23. The method according to claim 19,

Y being a structural component having an optical response property.

24. The method according to claim 19, the Formula (0) being represented as the following compound:

(I)

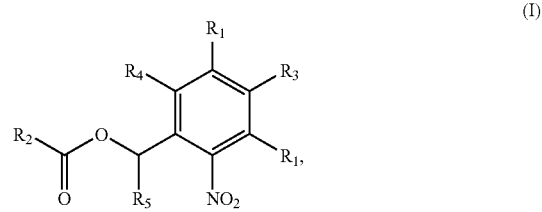

wherein:

$R_1$ independently represents a hydrogen atom, $-OR_6$ ($R_6$ is an alkyl chain having a carbon number of 1 to 10), $-NH(CO)R_7$ ($R_7$ represents an alkyl chain having a carbon number of 1 to 10, or an alkyl fluoride chain having a carbon number of 1 to 10), $-N(R_8)_2$ ($R_8$ represents an alkyl chain having a carbon number of 1 to 5) or $-S(R_9)$ ($R_9$ represents an alkyl chain having a carbon number of 1 to 10);

$R_2$ represents an N-hydroxy succinic imide group (optionally substituted with a sulfonyl group);

$R_3$ represents $-X_2-(CH_2)_n-X_1$, wherein $X_2$ represents $-CH_2-$ or $-O-$, n is 0 or an integer of 1 to 10, and $X_1$ represents $-OZ$, -Z or

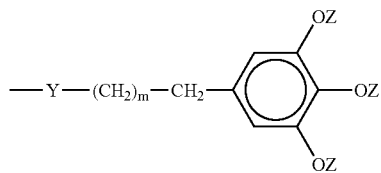

wherein:

Y represents $-(CH_2)-$ or $-O-$, Z represents a fluoroalkyl group having a carbon number of 1 to 20 and m represents 0 or an integer of 1 to 10;

$R_4$ represents $-NO_2$ or a hydrogen atom; and $R_5$ is a hydrogen atom or an alkyl group having a carbon number of 1 to 10.

25. The method according claim 19, further comprising: a step of fixing a compound having a functional moiety, which is capable of bonding X, onto the solid-phase surface before ejecting a liquid including a compound represented as the compound (I).

26. The method according to claim 19, the method of ejecting a droplet being an ink-jet method.

27. The method according to claim 19, the droplet including a solvent, which is selected from any of groups, such as water, ethanol, DMF, DMSO, HMPA, pyrrolidone group, and dioxane.

28. The method according to claim 19, the method of ejecting a droplet including a device that controls the drying of the droplet.

* * * * *

UNITED STATES PATENT AND TRADEMARK OFFICE
CERTIFICATE OF CORRECTION

PATENT NO. : 7,479,362 B2  Page 1 of 1
APPLICATION NO. : 11/116265
DATED : January 20, 2009
INVENTOR(S) : Hitoshi Fukushima et al.

It is certified that error appears in the above-identified patent and that said Letters Patent is hereby corrected as shown below:

On the Title Page, Item (75) Inventors

Please replace the seventh listed inventor name on the first page,

J.P. Jeyadevan

With

Jeyaratnam Prince Jeyadevan

Signed and Sealed this

Twenty-sixth Day of May, 2009

JOHN DOLL
*Acting Director of the United States Patent and Trademark Office*